US005674518A

United States Patent [19]
Fajt

[11] Patent Number: 5,674,518
[45] Date of Patent: Oct. 7, 1997

[54] METHOD OF FISH MANAGEMENT BY POISON FISH BAIT METHOD OF MAKING THE BAIT, AND FORMULATION OF BAIT

[75] Inventor: James R. Fajt, Auburn, Ala.

[73] Assignee: Prentiss Incorporated, Floral Park, N.Y.

[21] Appl. No.: 426,898

[22] Filed: Apr. 21, 1995

Related U.S. Application Data

[63] Continuation-in-part of Ser. No. 201,058, Feb. 24, 1994, which is a continuation of Ser. No. 741,061, Aug. 6, 1991, abandoned.

[51] Int. Cl.$^6$ ................................................. A01N 25/08
[52] U.S. Cl. ........................... 424/408; 424/406; 424/407; 424/410; 514/65
[58] Field of Search ................................. 424/405–410, 424/84, 417–420; 514/65

[56] References Cited

U.S. PATENT DOCUMENTS

| | | | |
|---|---|---|---|
| 2,884,356 | 4/1959 | Starr et al. | |
| 3,056,723 | 10/1962 | Galloway | 167/42 |
| 3,152,953 | 10/1964 | Strong et al. | 167/46 |
| 3,602,194 | 8/1971 | Marking | 119/3 |
| 4,174,406 | 11/1979 | Bordenca | 424/325 |
| 4,221,782 | 9/1980 | MacPhee et al. | 424/127 |
| 4,395,969 | 8/1983 | Cheng et al. | 119/3 |
| 4,563,344 | 1/1986 | Kotz | 424/17 |
| 4,731,247 | 3/1988 | Wolford et al. | 426/1 |
| 4,871,541 | 10/1989 | Shibanai | 424/411 |
| 4,874,611 | 10/1989 | Wilson et al. | 424/410 |
| 4,906,472 | 3/1990 | Gasseling et al. | 424/405 |
| 4,927,643 | 5/1990 | D'Orazio et al. | 426/1 |
| 4,992,275 | 2/1991 | Lush | 424/408 |
| 5,089,277 | 2/1992 | Prochnow | 426/1 |
| 5,135,744 | 8/1992 | Alexander et al. | 424/78 |

OTHER PUBLICATIONS

Brook, Price, *Studies on the Chronic Toxicity of Pro-Non-fish, a Proprietary Synergized Rotenone Fish-Toxicant*, 1960, pp. 49–56, Published in 1961.

Jun-ichi Fukami, *The Selective Toxicity of Rotenone Between Mammal, Fish and Insect*, 1969, p. 1970, Biochemical Toxicology of Insecticides.

Jun-Ichi Fukami, *Oxidative Metabolism of Rotenone in Mammals, Fish, and Insects and Its Relation to Selective Toxicity*, Nov. 12, 1969, pp. 1217–1226, Journal of Agricultural and Food Chemistry.

I. Yamamoto, *Mode of Action of Natural Insecticides*, 1969, pp. 161–174, Residue Reviews.

Primary Examiner—Neil S. Levy
Attorney, Agent, or Firm—Nolte, Nolte and Hunter, P.C.

[57] ABSTRACT

A piscicide formulation is combined with fish feed and a target species attractant to form poison oral bait pellets. The pellets are formed to a size and located in the aqueous environment of a fish population in a manner effective in selectively exterminating the target species by ingestion and not by poisoning the aqueous environment.

25 Claims, 1 Drawing Sheet

METHOD OF FISH MANAGEMENT BY POISON FISH BAIT METHOD OF MAKING THE BAIT, AND FORMULATION OF BAIT

This is a continuation-in-part of Ser. No. 08/201,058, filed Feb. 24, 1994, pending which is a continuation of Ser. No. 07/741,061, filed Aug. 6, 1991, abandoned.

BACKGROUND OF THE INVENTION

This invention concerns an improvement in the control of fish populations by taking advantage of the feeding habits of undesirable species of fish to selectively poison them. A wide variety of piscicides have been developed for use in fish management such as rotenone and juglone. It has long been known, however, that rotenone kills desirable as well as undesirable species of fish. Hence, the general procedure when a fish management has been overrun with undesirable species has been to destroy the entire fish population and reintroduce the desired species.

To avoid this Draconian solution, much of the prior art has concerned itself with developing toxicants which are specific to certain species, such as terpenzlaminoalkanol toxicants, U.S. Pat. No. 4,174,406; azide radicals, U.S. Pat. No. 4,221,782; and diethyl esters of phosphoric, phosphorous, thiophosphonic and thiophosphorous acid containing a chloride or vinyl group, U.S. Pat. No. 4,395,969. Unlike rotenone, these chemicals do not occur naturally and the environmental effects of their degradation products are unknown. Furthermore, desirable as well as undesirable species are exposed to these toxicants, though only the former are exterminated. What trace quantities may remain in desirable species and what effect this may have upon organisms higher in the food chain is unknown.

The present invention makes use of an oral poison or toxicant fish bait to take advantage of the feeding behavior of undesirable fish species such as common carp, grass carp, sunfish, bullhead, and suckers. The basis for the selectivity of oral poison fish bait is that different fish species have food preferences and/or will feed in unique ways and/or locations. This solves one of the most common problems fisheries managers face—the removal of some or all of a problem specie without harm or exposure to desirable game fish.

Because an oral poison fish bait kills fish on a dose-per-fish basis and not by environmental poisoning, the fishery's manager may add a controlled amount of poison fish bait to the water area and know before treatment the potential fish kill. Also, by using a preferred water-insoluble toxicant such as rotenone in the oral bait, and treating it and/or locating it for consumption by the target fish. There is little statistical chance of poisoning the aqueous environment and killing non-target fish.

OBJECTS OF THE INVENTION

It is an object of this invention to control undesirable species of fish in a population by specifically delivering a toxicant for alimentary digestion by those fish only.

It is a further object of this invention to permit the user to base his selection of a piscicide for fish management purposes upon criteria other than selectivity for a certain species, such as safety, cost, and environmental harmlessness.

SUMMARY OF THE INVENTION

Poisonal oral fish bait pellets are to target a specific species of fish by taking advantage of one or more of the criteria:

(1) what the target species of fish will consume,
(2) the size of the pieces or pellets of bait that the target species normally will consume,
(3) the aqueous location the target species normally feeds at and
(4) optionally but preferably training the fish to feed at a specific time and location.

DETAILED DESCRIPTION OF THE INVENTION

Figure 1:
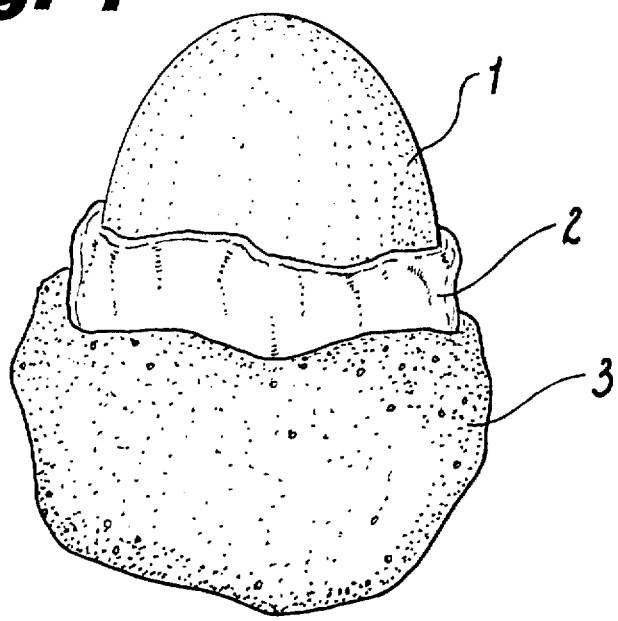
FIG. 1 is a cut-away view of a poison bait pellet.

In the preferred embodiment poison bait pellets, one of which is shown in FIG. 1, are created. The core 1 of the pellet contains the toxicant either in its solid form or, in the case of liquid toxicants, absorbed into a solid matrix, preferably common fish food. The preferred cores are commercially available feed pellets which are easily soaked in a liquid toxicant.

The core may also be coated with a water resistant gel layer 2 to prevent leaching of the toxic formulation into the aqueous environment. Coating may be performed by spraying or immersion or other well known methods. Encapsulating or coating is well know in the art of extrusion processing where an annular concentric orifice delivers a coating to an extruded column from an enclosed central orifice. Spraying or immersion are known methods. Another well known method of providing water resistance is to add an hydrophobic material to the mix, e.g. a fat or oil. Encapsulating the entire core is a fish-food layer 3 that may be simple fish-food but is preferably an attractant selective for the target species.

The buoyancy of the poison bait pellet may be used to control its vertical displacement in the aqueous environment. Lateral, as well as vertical, displacement may be controlled by feed retention devices such as 4 of FIG. 2. Many fish feeders are commercially available. Extrusion processes are known for introducing air bubbles to control specific gravity or buoyancy.

In my preferred embodiment, the toxicant used was rotenone. Rotenone has many advantages as a piscicide:

(1) at the level of proposed use, it does not threaten mammalian species,
(2) it is photodegradable,
(3) it is a natural extract of cube and derris roots and craca? vogelii and degrades in the environment,
(4) it has long been approved by the E.P.A. for fish control and,
(5) it is water-insoluble, hence leaching into the aqueous environment from the bait core is virtually undetectable.

Negative or positive buoyancy of the poison bait pellet is controlled by the feed pellet used for the core. Commercially available feed pellets that are produced by a heat extrusion process have air bubbles trapped inside them which cause the poison bait pellet to float. Feed pellets made by other processes usually sink.

A floating form of poison fish bait can be produced with a conventional pelleting machine. Normally a pelleting machine produces feed pellets by compacting the feed. This process produces a feed pellet negatively buoyant in water. To overcome this problem, I have developed a technique that incorporates dry ice in the production of the feed. Mixed with the feed, the dry ice will be trapped in the pellet as it is produced. The trapped dry ice will rapidly warm and sublimate to CO2 gas, leaving microcavities in the pellet. This space of trapped air will increase the buoyancy of the pellet and allow it to float. Dry ice is added at a rate of 2–5% of the total feed weight.

Figure 2:
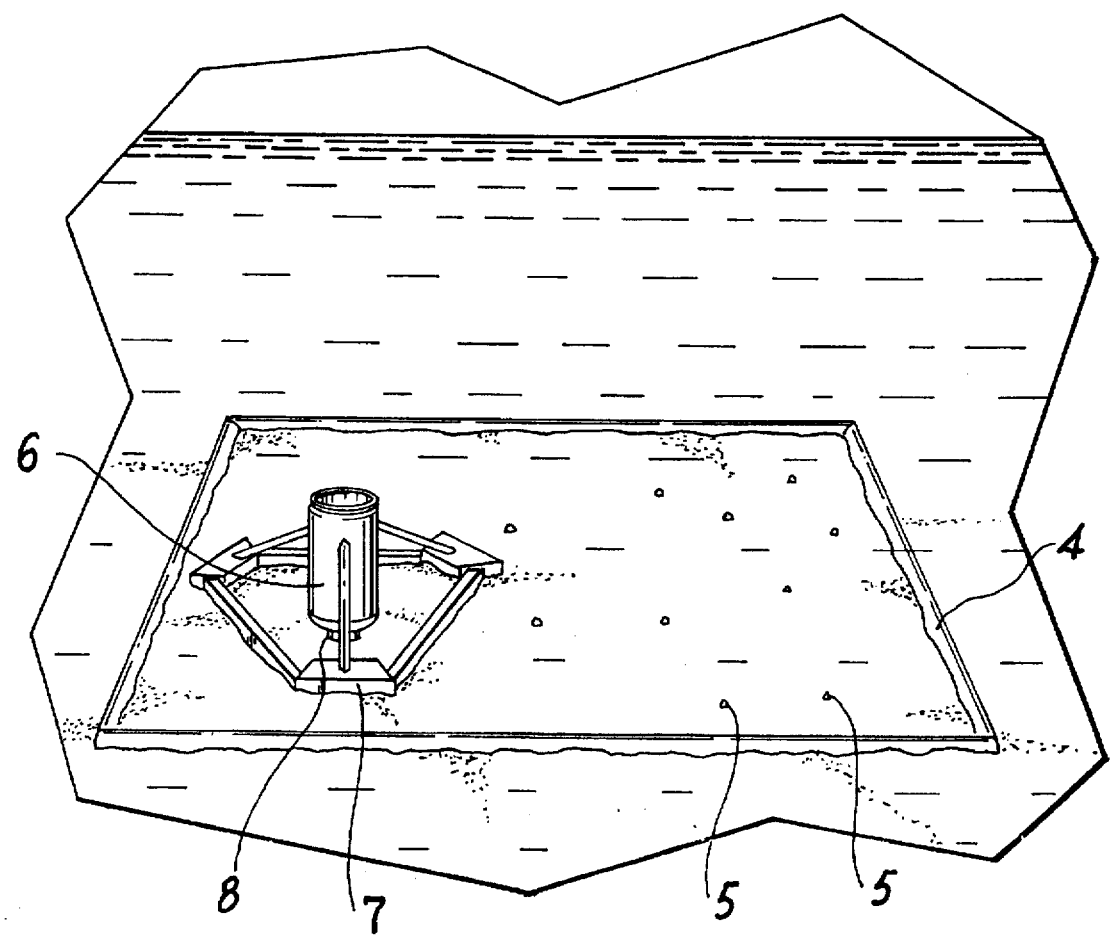
FIG. 2 is a pictorial view of the method of the invention.

FIG. 2 shows a feed retention device 4 floating in an aqueous environment and retaining positively buoyant poison bait pellets 5. Also shown is a feeder 6 having a timer-actuated dispenser mechanism 8. The feeder I use is actually a commercially available turkey feeder which I have modified by adding floats 7. At regular pre-set intervals, the dispenser mechanism 8 releases a fixed quantity of the poison bait pellets into the retention area.

One of rotenone's greatest advantages is its commercial availability. Cube root extract having 30–50 percent active rotenone is readily available. In my formulations I use a rotenone resin that is produced by Prentiss Drug and Chemical Co., Inc. of Floral Park, N.Y. and is reported to be 47 percent active rotenone. Therefore, a formulation having 6 percent rotenone resin by weight will have 2.8 percent active rotenone by weight.

Finely powdered rotenone resins, when administered orally, will kill fish in the dosage range of 50–100 mg of resin per kilogram of fish body weight. Raw powder cube root is effective in the range of 40–80 mg/Kg.

When combined with a synergist, the toxicity of rotenone is nearly doubled. Preferred synergists are 2-(2-ethoxyethoxy) ethyl 3,4-(methylenexioxy) phenyl acetal of acetaldehyde, which goes by the generic name of sesamex; 1,2-(methylenedioxy)-4-[2-(Octylsulfinyl)propyl]benzene, also known as sulfoxide; alpha-[2-butox-yethoxy)-ethoxy]-4,5-(methylenedioxy)-2-propyltoluene, also known as piperonyl butoxide; dipropyl 5,6,7,8-tetrahydro-7-methylnaphtho[2,3-d]-1,3-dioxole -5,6-dicarboxylate, also known as n-propyl isome; 3-alkyl-6-carbethoxy-5-(3,4-methylenedioxyphenyl)2-Cyclohexen-1-one mixed with 3-alkyl-5-(3,4-methylenedioxphenyl)-2-Cyclohexen-1-one, also known as piperonyl cyclonene; and B-diethylaminoethyl diphenylpropyl acetate HCL, also known as SKF-525A.

I have discovered that the killing effectiveness of rotenone is greatly increased when combined with a synergist and an adsorption agent or agents. Surfactants are effective adsorption agents in that they break down the surface tension of membranes on the lining of the fish's stomach and allow for greater penetration of the toxic rotenone. Surfactants useful for this purpose include sorbitan derivatives, cyclodextrin, simethicone, sodium lauryl sulphate, and dioctyl sodium sulfosuccinate.

Also, though conventional wisdom teaches that rotenone is incompatible with alkali, I have discovered that small amounts of base ned as metal hydroxides, alkali buffer solutions such as carbonates, phosphates, acetates, borates and phthalates, or other antacids increase the effectiveness of rotenone by neutralizing the digestive acids of the target fish, thereby retarding acid hydrolysis of the toxin and aiding in the [absorption] of the toxin through the stomach lining. Chelating agents have also proven successful in increasing adsorption. Hydrophobic materials, such as oils, are also effective in increasing adsorption. I group all such compounds as absorption agents. Effective absorption agents are sodium hydroxide, aluminum hydroxide, sodium carbonate, sodium bicarbonate, potassium hydroxide, EDTA (ethylenediaminetetracetic acid), codliver oil, mineral oils, vegetable oils and the surfactants previously mentioned.

The pH of a drug or toxicant is important in determining the absorption of a toxic agent. Rotenone must enter the body of the fish to kill. Research has shown that rotenone will only enter the body of the fish through the gills when used as an emulsified product. To enter the body of the fish, it must be lipid soluble or, in other words, it must be soluble in the tissues of the fish. For rotenone to be lipid soluble, it must be in a non-ionic state. The ionic state of the rotenone molecule like any other is effected by the acid or base content of the environment in which it is located. So the pH of the solution is very important. Conventional wisdom and 50 years of field testing show that rotenone is more effective at neutral pH values. This is because rotenone remains in the Don-ionic state at neutral pH values and is, therefore, more lipid soluble. My work on rotenone as a stomach poison has shown that rotenone's solubility in the gastrointestinal tract is enhanced by buffering the pH of the feed at a high pH of 8–10. What this high pH buffering does is counteract the low or acidic pH of the fish stomach. This results in a more neutral pH of the gastrointestinal tract and increases the lipid solubility of the molecule and decreases the amount of rotenone needed to kill the fish.

Sorbitan is in a class of compound known as surfactants. Surfactants decrease the surface tension of membranes and increase absorption. There are tens of thousands of surfactants that can be used. I have listed the ones that have been tested.

EDTA is a chelating agent that binds to divalent cations. Pharmacological references indicate that it functions to increase the permeability of cell membranes. By increasing the permeability of the membranes, it will act as an absorptive agent.

Cyclodextrine is a cyclic form of dextrin that is used as an absorptive agent. The structure of the cyclodextrine ring allows for the formation of micelles with the rotenone molecule. A micelle formed is absorbed through the stomach lining of the fish better than the rotenone molecule alone. Once in the bloodstream of the fish, the micelle is easily broken and the rotenone is released to have its toxic action. The cyclodextin is also a formulation aid in that it prevents rotenone from recrystallizing in the feed, therefore, keeping the size of the rotenone particles as small as possible and increasing absorption. Rotenone-cyclodextrin micelles are made by dissolving the rotenone in ethanol. The cyclodextrin is dissolved in warm water. The two liquid portions are put together in formula weight ratios that range from 3-1 to 1-1 rotenone to cyclodextrin. This is part of the entire rotenone solution that the feed is soaked in to produce the poison fish food.

A typical formulation for a 300 mg core would be as follows:

| | |
|---|---|
| Cube Root Resin | 22 mg |
| (10 mg active rotenone) | |
| Synergist | 2 mg |
| Adsorption Agent | 7 mg |

Of course, in formulations having more active rotenone, the amounts of synergist and adsorption agent are increased proportionally.

These substances are dissolved in an organic solvent (ethanol, methanol, isopropanol, acetone, or ether) and soaked into or sprayed on commercially available feed pellets. The feed pellets are then coated with an attractant layer to form the poison bait pellet.

An attractant coating is prepared as follows:

| Water | 89% by weight |
|---|---|
| Fish attractant | 7% by weight |
| Binder | 4% by weight |

Suitable binders include gelatine, agar, KELGIN™, algin potato starch, konjack flower, gum karaya, gum guar, and cellulose gum. Such binders, oils or fats may also serve to coat the pellet for water resistance, particularly if a water soluble poison is employed. KELGIN® is a trademark of Merckh & Co. of Rahway, N.J., a hydrophillic colloid of algin compounds extracted from brown algae.

Another method of creating the bait is to introduce a rotenone formulation directly into a heat extrusion process. I have determined that rotenone can withstand exposure to temperatures of 150° C. for more than one hour without significant degradation. This will allow for the production of floating poison fish bait with a conventional feed extruder. The heat extrusion process of floating feed production operates at a temperature range of 100°–129° C. In this type of processing, the rotenone formulation would be mixed in with the rest of the feed ingredients before the feed pellet is heat extruded to produce a floating pellet. An antioxidant is added to aid in the preservation of the rotenone-laced feed. The preferred antioxidant is ethoxyquin (1,2-dihydro-6-ethoxy-2,2,4-trimethylquinoline) that is approved for fish feed at a rate of 150 mg/kg of feed.

The size and location of the poison bait pellets, as well as the preferred minimum quantity of active rotenone per kilogram of fish body weight, are summarized as follows:

| TARGET SPECIES ROTENONE/KG | POISON BAIT PELLET SIZE | AQUEOUS LOCATION | MINIMUM ACTIVE |
|---|---|---|---|
| Common Carp | 2–5 cm. | Surface | 20 mg./kg. |
| Grass Carp | 2–5 cm. | Surface | 10 mg./kg. |
| Blue Gill | 0.1–1 cm. | Bottom or Surface | 10 mg./kg. |
| Bullhead | 2–6 cm. | Bottom | 15 mg./kg. |
| Sucker | 0.25–1 cm. | Bottom | 10 mg./kg. |
| Tilapia | 1–4 cm. | surface | 20 mg./kg. |

Tests have shown that it is advantageous and desirable to train fish to feed on the bait pellets. Fish have a home ranging behavior where different groups of the same species respond to feeders at various locations. In a series of tests targeting sterile triploid grass carp, floating feeders were anchored 20 to 50 meters from the edge of emergent vegetation or shoreline in a lake in water depths of 1 to 3 meters. Buoyant pellets were prepared with desirable food and attractant and containing everything except the toxin rotenone. The training pellets were of small nugget size and dispensed twice a day in quantities ranging from 250 to 400 grams. After the feeding response was initiated and stabilized generally requiring a period of 10 to 25 days, 125 to 300 grams of pellets containing active rotenone about 10 milligrams per kilogram bait pellets were dispensed. On the follow day the dead fish were counted using the Peterson method (Ricker, W. E. 1975 Computation and Interpretation of Biological Statistics of Fish Populations. Bulletin Fishery Research Board of Canada 191,382p.). Recovery rates from 50 to 100% averaging 84% were obtained. The formula used in the Peterson method is N=M×C/R where N equals the estimated number killed, and M the number marked first day, C equals number of fish collected the second day, and R number of marked fish collected the second day. The marked fish had been previously collected with landing nets, marked with fin clips and returned to the lake. Non-target fish found dead during 72 trials total 16 or an average of about 1 fish in every 5 trials. No effects on non-piscine wild life were observed. Species present included otter, alligator, Florida soft-shell turtle, bald eagle, osprey, anhinga, black vulture, turkey vulture, sandhill crane, great blue heron, common egret, snowy egret, swallow-tale kite, common grackle, and common gallinule.

Grass carp and common carp both feed on the surface at a fish feeder and are typically the first and largest fish to come to the feeder in a fish population. The size of the floating poison bait pellets in the range of 2–5 cm. will restrict other forms of fish from feeding on the bait. Both types of carp seem to prefer fish food that contains some type of bread meal. A formulation of fish feed that contains yeast or bread crumbs is a preferred attractant.

Blue Gill frequently become a problem in fisheries when they overpopulate and do not grow to desirable size. To be selective for blue gill, the poison bait pellets are in the 0.1–1 cm. range so the smaller fish in the Blue Gill population will eat them. Blue Gills tend to feed off the bottom of the aqueous environment so a poison bait pellet that sinks is more selective for this species, but this species is also known to feed from the surface on occasion. Amino acids and nucleotides can be used as attractive agents for feeds. These amino acids and nucleotides are what tell the fish through its chemo receptors in the mouth that it has a food item it can eat. So by incorporating the specific amino acids and nucleotides in the feed that blue gill know as feed items, it is possible to attract them to the feed. The preferred amino acids are betaine, proline, glycine, and the preferred nucleotides are AMP (adensine monophosphate) and IMP inosine monophosphate.

Bull Head are bottom feeders that rely on their sense of smell to locate food. The attractant of choice is heavy fish oil, fish meal, blood meal, or beef by-products. The poison bait pellets should sink and have a relatively large size of 2–6 cm.

Sucker species are largely bottom feeders that feed on invertebrates. A soft sinking poison bait pellet of small size in a range of 0.5–1 cm. is preferred and the preferred attractant is round tubifix worms to simulate natural feeding habits.

Tilapia, like carp, are attracted to yeast and bread crumbs and feed at the surface. However, tilapia prefer pellets in the range of 1–4 cm in width.

Though rotenone is preferred, it is to be understood that my method of controlling fish populations is not limited to this toxin only. Other known toxins are juglone, antimycin A and toxaphene, for example. It is also known that various rotenone (metabolites)derivatives are toxic. These include 8'-hydroxyrotenolones I and II; 6',7'-dihydro-6',7' dihydroxyrotenolones I and II; 6',7'-dihydro-6',7' dihydroxyrotenone; 8'-hydroxyrotenone; and rotenolones I and II.

It is to be understood that there are many variants of the described methods, apparatuses, and formulations and that the scope of the invention is to be limited only to the scope of the claims herein.

I claim:
1. A method for controlling target species of fish populations in aqueous environment, said method comprising:
   forming a pellet of fish food said pellet being selectively sized for the target species and said fish food having an attractant being selectively targeted for said species,
   forming a piscicide formulation toxic to the target species of the fish population, said piscicide formulation com- prises a toxicant from the group consisting of rotenone: 8'-hydroxyrotenolone I; 8' hydroxyrotenolone II; 6',7'-dihydro-6',7' dihydroxyrotenone I; 6',7'-dihydro-6',7'-dihydroxyrotenone II; 6',7'-dihydro-6',7'-dihydroxyrotenone; 8'-hydroxyrotenone; rotenolone I; rotenolone II; juglone, antimycin A; and toxaphene, uniting said piscicide with said fish food pellet to inhibit said piscicide from leaching into water when said pellet is placed in an aqueous environment, incorporating said feed pellet with an attractant effective to selectively attract said target species, selectively placing said pellet with said united fish food and piscicide in an aqueous environment containing a fish population in a position to exterminate the target species by oral consumption and digestion of said pellet.

2. The method of claim 1 wherein said piscicide formulation further comprises a synergist from the group consisting of sesamex, sulfoxide, piperonyl butoxide, n-propyl isome, piperonyl cyclonene, and SKF-525A.

3. The method of claim 1 wherein said piscicide formulation further comprises an adsorption agent from the group consisting of sorbitan, cyclodextrin, simethicone, sodium lauryl sulphate, dioctyl sodium, sulfosuccinate, alkali, alkali buffer, antacid, cod liver oil, vegetable oil, mineral oil, and ethylenediaminete tracetic acid (EDTA).

4. The invention of claim 1 wherein: said fish food pellet is united with said piscicide by:

dissolving said piscicide formulation into a solvent to form a solution; and soaking said solution into said feed pellet.

5. The method of claim 4 further comprising:

incorporating said attractant by coating said feed pellet with the attractant effective to selectively attract said target species.

6. The method of claim 1 wherein said coating is formed by:

mixing said attractant with water and a binder from the group consisting of gelatin, agar, KELGIN®(a hydrophillic colloid of algin compounds extracted from brown algae), algin, potato starch, konjack flower, gum karaya, gum gura, and cellulose gum; and coating said feeding pellet with said mixture and allowing it to set.

7. The method of claim 5 wherein said coating is formed by:

mixing said attractant with water and a binder from the group consisting of gelatin, agar, KELGIN®(a hydrophillic colloid of algin compounds extracted from brown algae), algin, potato starch, konjack flower, gum karaya, gum gura, and cellulose gum; and coating said feeding pellet with said mixture and allowing it to set.

8. The method of claim 1 wherein said attractant is from the group consisting of yeast and bread and the target species is from the group consisting of common carp, grass carp, and tilapia.

9. The method of claim 1 wherein said attractant is from the group consisting of fish oil, fish meal, blood meal, and beef by-products and the target species is bull head.

10. The method of claim 1 wherein said attractant is tubifix worms and the target species is sucker.

11. The method of claim 1 wherein said attractant is from the group consisting of glycine, proline, betaine, adenosine monophosphate (AMP) and inosine monophosphate (IMP) and the target species is blue gill.

12. The method of claim 1 wherein:

said united pellets are 2–5 cm wide, said pellets are positioned at the surface of the aqueous environment, and said target species is from the group consisting of common carp and grass carp.

13. The method of claim 1 wherein: said pellets united with piscicide are 0.1–1 cm. wide, and said target species is blue gill.

14. The method of claim 1 wherein:

said pellets united with piscicide are 2–6 cm wide, said pellets are positioned at the bottom of the aqueous environment, and said target species is bullhead.

15. The method of claim 1 wherein:

said pellets united with piscicide are 0.25–1 cm. wide, said pellets are positioned at the bottom of the aqueous environment, and said target species is sucker.

16. The method of claim 1 wherein:

said pellets united with piscicide are 1–4 cm. wide, said pellets are positioned at the surface of the aqueous environment, and said target species is tilapia.

17. The method of claim 1 further comprising:

coating said food pellet and its united piscicide with a water resistant layer.

18. The method of claim 17 wherein said water resistant layer is taken from the group consisting of a gel, agar, KELGIN®, algin, starch, gums, fats and oils.

19. A method according to claim 1 for controlling target species of fish populations in an aqueous environment said method comprising:

forming pellets of fish food said pellets being selectively sized for the target species and said fish food being selectively targeted for said species, placing said pellets in a selected location at preselected times to train said target species to feed on said pellets, forming a piscicide formulation toxic to the target uniting said piscicide with said fish food pellets and placing said pellets in said preselected place at preselected times to selectively kill a substantial number of said target specie by oral consumption of said pellets.

20. The method of claim 1, wherein said piscicide formulation includes an antioxidant.

21. The method of claim 20, wherein said antioxidant is ethoxyguin.

22. The method of claim 1, wherein said piscicide formulation further comprises an adsorption agent.

23. The method of claim 1, wherein said piscide is a liquid formulation and is absorbed into said food pellet.

24. The method of claim 1 wherein said food pellet is further coated with an hydrophobic substance to prevent leaching into water.

25. A pellet produced by the method of claims 1, 2, 3, 4, 6, or 18.